(12) United States Patent
Baumfalk et al.

(10) Patent No.: US 7,674,254 B2
(45) Date of Patent: Mar. 9, 2010

(54) CONNECTOR, CONNECTOR SYSTEM, AND USE THEREOF

(75) Inventors: Reinhard Baumfalk, Gottingen (DE); Uwe Becker, Dransfeld (DE); Oscar-Werner Reif, Hannover (DE)

(73) Assignee: Sartorius Stedim Biotech GmbH (DE)

( * ) Notice: Subject to any disclaimer, the term of this patent is extended or adjusted under 35 U.S.C. 154(b) by 189 days.

(21) Appl. No.: 11/655,442

(22) Filed: Jan. 19, 2007

(65) Prior Publication Data

US 2007/0185472 A1 Aug. 9, 2007

(30) Foreign Application Priority Data

Feb. 7, 2006 (DE) ........................ 10 2006 005 533

(51) Int. Cl.
*A61B 19/00* (2006.01)
*A61M 25/16* (2006.01)
*A61M 25/18* (2006.01)

(52) U.S. Cl. ....................... 604/533; 604/403

(58) Field of Classification Search ......... 604/403–416, 604/533–539; 285/3, 4, 260, 332, 352, 423; 128/214; 435/297.1
See application file for complete search history.

(56) References Cited

U.S. PATENT DOCUMENTS 4,187,846 A * 2/1980 Lolachi et al. .............. 604/411
6,379,340 B1 * 4/2002 Zinger et al. ................ 604/246
7,303,544 B2 * 12/2007 Butikofer et al. ......... 604/93.01
2005/0239198 A1 * 10/2005 Kunas et al. ............. 435/297.1
2006/0252298 A1 11/2006 Biddel et al.

FOREIGN PATENT DOCUMENTS

DE 34 04 639 8/1985
DE 42 07 845 9/1993
DE 10 2005 030 318 A1 1/2007

* cited by examiner

*Primary Examiner*—Leslie R Deak
*Assistant Examiner*—Philip R Wiest
(74) *Attorney, Agent, or Firm*—Gerald E. Hespos; Anthony J. Casella

(57) ABSTRACT

A connector (10) is provided for sterile connection to a complementary connector (12). The connector (10) has a housing (14) with an engagement device (16) to engage a complementary engagement device (18) of the complementary connector (12) along an engagement direction (44). The connector (10) is displaceable relative to the complementary connector (12) along the engagement direction (44) after the engagement device (16) engages the complementary engagement device (18). The housing (14) has a feed-through opening (24) for receiving a sensor (34) and a cover (22). The cover (22) is displaced relative to the connector (10) along the engagement direction (44) to close the feed-through opening (24) in a sterile manner. The connector (10) also has a sterile sensor (34) that is movable along a sensor displacement direction (52) that differs from the engagement direction (44).

13 Claims, 6 Drawing Sheets

CONNECTOR, CONNECTOR SYSTEM, AND USE THEREOF

BACKGROUND OF THE INVENTION

1. Field of the Invention

The present invention relates to a connector for sterile connection to a complementary connector, to a connector system for sterile connection of a feed-through opening of a connector to a fluid inlet and/or fluid outlet of a conventional connector, and to the use of a connector and of a complementary connector for sterile connection of a feed-through opening of the connector to a fluid inlet and/or fluid outlet of the complementary connector.

2. Description of the Related Art

In modern pharmaceutical technology and/or laboratory technology, use is frequently made of containers, such as, for example, bags, flexible tubes bioreactors, etc., in which bioprocesses, and chemical, biochemical, etc. reactions take place. In particular, these reactions take place in a closed environment, i.e. without connection to a surrounding medium. It is necessary in this case to avoid germs from the environment penetrating the interior of above-mentioned containers and impairing and distorting the progress of reactions, experiments, etc. Furthermore, containers of this type may be used in hospital environments, for example for blood transfusion and blood washing. In this case too, care has to be taken to ensure that germs from the environment do not penetrate the interior of a container, since, for example, the content of the container could be contaminated as a result.

Many of the processes taking place in these preferably flexible containers should, if possible, take place under predetermined or controlled conditions. For this purpose, it may be necessary, for example, to detect and/or to measure physical variables or values of the media present in the containers. For example, it may be necessary to measure variables, such as temperature, pH value, cell density, optical transmission, etc., wherein these values are to be measured as directly as possible without running the risk of contaminating the interior of the container.

It is therefore an object to determine physical and/or chemical and/or other parameters in the interior of a container in a simple manner without the interior of the container entering into contact with a surrounding medium.

SUMMARY OF THE INVENTION

According to one aspect of the invention, a connector for sterile connection to a complementary connector comprises a connector housing with an engagement device that is designed to enter into engagement with a complementary engagement device of the complementary connector essentially along an engagement direction. The connector is displaceable relative to the complementary connector essentially along the engagement direction after the engagement device enters into engagement with the complementary engagement device. The connector further includes a feed-through opening for feeding a sensor device therethrough. A displaceable, sterile covering device is designed to close the feed-through opening in an essentially sterile manner. The covering device is displaced relative to the connector essentially along the engagement direction when the connector is displaced relative to the complementary connector. The connector further includes an essentially sterile sensor device that is movable essentially along a sensor displacement direction. The engagement direction differs from the sensor displacement direction.

For example, the sensor device can be essentially cylindrical, and the sensor displacement direction can be essentially parallel to an axis of symmetry of the sensor device, in particular a cylinder axis of the sensor device. The engagement direction can preferably be essentially perpendicular with respect to the sensor displacement direction.

The term "essentially cylindrical" within the meaning of the invention comprises, for example, production-induced deviations from the cylindrical shape. In particular, the sensor device may not have a circular shape in cross section with a constant radius, but rather, as expressed in cylindrical coordinates, different radii given different solid angles. In particular, given different solid angles, the actual radius may differ from the radius of the circular shape by approximately 20%, in particular by approximately 10% or less.

The term "displaceable essentially along the engagement direction" within the meaning of the invention comprises the fact that, for example, the connector and the complementary connector are displaceable precisely along the engagement direction. However, during the displacement, there may be a deviation from the engagement direction. For example, the connector may be displaced relative to the complementary connector along a direction which differs from the engagement direction, for example is at an angle of about 1° to about 20°, preferably about 3° to about 10° with respect to the engagement direction. The direction at which the connector is displaceable relative to the complementary connector may also be askew with respect to the engagement direction.

If the sensor device is pushed or moved along the sensor displacement direction through the feed-through opening, the sensor device can enter into engagement with the complementary connector, in particular a fluid inlet and/or fluid outlet, as a result of which further displacement of the connector relative to the complementary connector along the engagement direction is prevented. The sensor device is therefore advantageously also a locking device.

The connector preferably is designed such that, when the sterile covering device is displaced, a sterile, complementary covering device of the complementary connector is also displaceable. Consequently, sterile regions of the connector only enter into contact with sterile regions of the complementary connector, i.e. the connection between the connector and the complementary connector is essentially sterile.

In this invention, the term "sterile" is used according to its conventional use, i.e. the term "sterile" covers, in particular, germ-free or sterilized or infertile. However, germ-free does not have to mean a complete absence of germs or foreign bodies. On the contrary, germ-free may contain a predetermined or predeterminable maximum number of germs or foreign bodies. For example, sterile may cover a maximum number of germs as permitted or desired in accordance with conventional industrial standards.

After the sterile connection between the connector and the complementary connector is produced, the sensor device can be at least partially introduced along the sensor displacement direction through the feed-through opening into the complementary connector. The sensor device can therefore enter into contact with an interior of the complementary connector or with an interior of an object to which the complementary connector is connected. For example, the complementary connector may be connected directly to a container. In other words, the fluid inlet and/or fluid outlet of the connector is connected directly to the container preferably in a sterile manner. The sensor can therefore be at least partially inserted into the interior of the complementary connector and/or into the interior of the container connected to the complementary connector. In particular, the sensor device can come into connection or contact with a medium in the container, for example a fluid, a liquid, a gas, etc. The sensor device can therefore advantageously directly measure or detect or determine physical properties of the fluid, the liquid, the gas, etc.

The container is preferably a bioreactor, a bag or a filter housing, particularly preferably a "filter capsule".

The sensor device may be, for example, an electric, an electronic, a mechanical, an optical, a chemical, etc., sensor device. The sensor device may be connected to an analyzing device by means of a cable, for example an electric cable, a glass fiber cable, etc. However, the sensor device may also be connected to an analyzing device without a cable. In this case, the analyzing device may be arranged outside the connector. However, the analyzing device may also be part of the sensor device, and the sensor device or the analyzing device may furthermore be equipped with a display device, in particular a digital display device, for example for displaying a temperature.

The sensor device may be movable, for example, manually and/or automatically along the sensor displacement direction. For example, a higher pressure may be present in the interior of the connector than in the interior of the complementary connector or of the container connected thereto. If the connector and the complementary connector are connected to each other in a fluidtight manner, the sensor device can be at least partially pushed or moved into the interior of the complementary connector or of the container connected thereto, for example, by equalization of the pressure. Alternatively, the pressure in the container can be increased and, as a result, the sensor device can be moved out of the container or the complementary connector again and back into the connector.

By means of the engagement device, the connector is fixable to the complementary connector essentially along the sensor displacement direction. Fixable along a predetermined direction within the meaning of this invention means, for example, that, during normal operating forces, a movement of the connector relative to the complementary connector in the predetermined direction is completely suppressed, or only a very limited movement in the predetermined direction is possible. The term "locking" or "lockable" is used essentially synonymously.

On account of the engagement device, the connector is therefore fixable or lockable to the complementary connector essentially along the sensor displacement direction. Furthermore, on account of the at least partial insertion of the sensor device into the complementary connector or the container arranged thereon, the connector is fixable or lockable to the complementary connector essentially along the engagement direction.

The connector is particularly preferably releasably fixable or lockable to the complementary connector.

Furthermore, the connection between the connector and the complementary connector is preferably fluidtight, i.e. an exchange of fluids or a communication of fluids with the environment is essentially not possible. However, an exchange of fluids between the connector and the complementary connector is possible. In particular, after the sensor device is removed from the complementary connector or from the container arranged thereon, the connector is displaceable relative to the complementary connector along or counter to the engagement direction, as a result of which the connector can be separated from the complementary connector.

The sensor device is preferably arranged within a sensor chamber which has an essentially sterile interior. In particular, the sensor chamber contains the feed-through opening.

Particularly preferably, the connector has an interior space, and the interior space is essentially identical to the sensor chamber.

Furthermore, the connector housing is preferably at least partially composed of a flexible material, and the connector housing is furthermore designed in such a manner that the volume of the sensor chamber can be varied. In particular, the size of the sensor chamber can be matched to the size of the sensor device.

The connector housing preferably is designed to be at least partially compressible and/or extendable, in particular the connector housing is designed such that it is expandable. The connector housing can therefore advantageously be matched to the size of the sensor device in a simple manner. For example, the connector housing can be at least partially squeezed manually and, in particular, force can be transmitted from the outside to the sensor device, as a result of which the sensor device can be movable manually or automatically into the interior of the complementary connector or of the container arranged thereon. In other words, the interior volume of the connector housing and of the sensor chamber are matchable, as a result of which an at least partial removal of the sensor device from the sensor chamber or the connector chamber can be compensated for.

The connector housing preferably is at least partially composed of a material capable of being reset. The connector housing may be manufactured, in particular, from different materials, for example from rigid and flexible materials. The connector housing may be composed, for example, at least partially of a rigid plastic and at least partially of a flexible material capable of being reset, such as, for example, a film, a rubber, a soft polymer, etc.

The connector is preferably designed, after arrangement or connection of the connector with or to the complementary connector, to connect the sensor chamber to an interior space of the complementary connector in an essentially sterile manner. In other words, a sterile connection of the interior space of the connector to the interior space of the complementary connector and the container arranged thereon can be produced without impurities or germs from the environment being able to penetrate the interior space of the complementary connector or of the container arranged thereon.

Furthermore, the connector housing is preferably designed to exert a force on the sensor device. For example, owing to the capability of the material of the connector housing to be reset, the connector housing may be prestressed. For example, the connector housing may be stretched and, on account of its capability of being reset, may endeavor to attain an unstretched state. In this case, a force can be transmitted to the sensor device. Particularly preferably, the sensor device can be pressed, for example, against the sterile covering device. If the sterile covering device is removed, then, owing to the force applied by the connector housing, the sensor device can be displaced or moved essentially along the sensor displacement direction. In an advantageous manner, when the connector is connected to the complementary connector, in the process the sensor device can automatically be at least partially pushed into the interior of the complementary connector or of the container arranged thereon, and the connector can be automatically locked at the same time to the complementary connector along the engagement direction.

The connector housing is therefore advantageously designed, after connection of the connector to the complementary connector, to move the sensor device at least partially into the complementary connector.

Particularly preferably, after removal of the covering device and of the complementary covering device, the sensor device is movable through the opening device into the interior space of the complementary connector.

A further aspect of the present invention comprises a connector system for sterile connection of a feed-through opening of a connector according to the present invention to a fluid inlet and/or fluid outlet of a conventional connector. The feed-through opening of the connector and the fluid inlet and/or fluid outlet of the conventional connector are preferably connected to each other in a fluidtight manner.

A further aspect of the invention relates to the use of a connector and of a complementary connector for sterile connection of a feed-through opening of the connector to a fluid inlet and/or fluid outlet of the complementary connector. The use preferably is carried out by providing the connector and the complementary connector; bringing an engagement device of the connector into engagement with a complementary engagement device of the complementary connector; displacing the connector relative to the complementary connector along an engagement direction and displacing the sensor device along a sensor displacement direction.

The connection of the feed-through opening of the connector to the fluid inlet and/or fluid outlet of the complementary connector is preferably fluidtight.

Furthermore, the sensor device is preferably pushed along the sensor displacement direction through the feed-through opening and at least partially into the fluid inlet and/or fluid outlet of the complementary connector.

The covering device of the connector and/or the complementary covering device of the complementary connector preferably are displaced along the engagement direction when the connector is displaced relative to the complementary connector.

Furthermore, the sensor device preferably is removed again from the complementary connector.

The connector preferably is separated from the complementary connector, and the connector, by means of the covering device, and/or the complementary connector, by means of the complementary covering device, is closed again in a fluidtight, furthermore preferably sterile, manner.

Furthermore, the above details concerning the connector or the complementary connector apply analogously also to the preferred use thereof according to the invention.

DETAILED DESCRIPTION OF THE PREFERRED EMBODIMENTS

Figure 1:
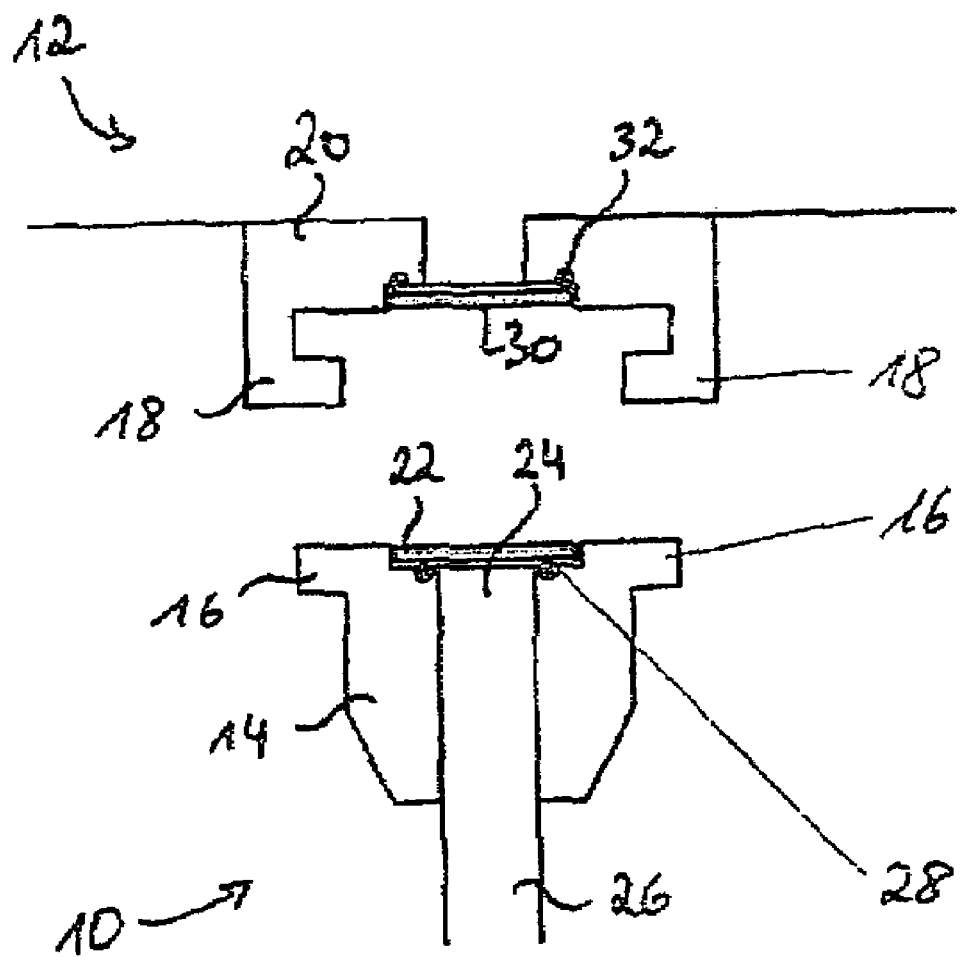
FIG. 1 shows a schematic sectional view of a preferred connector and of a complementary connector.

FIG. 1 shows a connector 10 and a complementary connector 12. The connector 10 has a connector housing 14. The connector housing 14 includes a projection 16. The projection 16 at the same time constitutes the engagement device 16. The engagement device 16 can enter into engagement (not illustrated) with a complementary engagement device 18 of a complementary connector housing 20 of the complementary connector 12. Furthermore, a germ barrier in the form of a sterile covering 22 is arranged on the connector housing 14. The sterile covering 22 can be designed, for example, as a slide. The sterile covering 22 covers, in particular, a feed-through opening 24 of an interior space 26 of the connector housing 14 of the connector 10. Furthermore, a sealing means 28 is arranged in the form of an O-ring 28. The O-ring 28 permits a fluidtight connection of the connector housing 14 to the sterile covering 22 when the engagement device 16 and the complementary engagement device 18 are in engagement.

Analogously, the complementary connector 12 has a complementary, sterile covering 30 in the form of a slide. Similarly, the complementary connector housing 20 of the complementary connector 12 has a sealing means 32 in the form of an O-ring 32. The O-ring 32 permits a fluidtight and sterile connection between the sterile covering 30 and the complementary connector housing 20 of the complementary connector 12. The O-rings 28, 32 may be essentially the same size. The O-rings 28, 32 may also differ in size. Consequently, in the use position of the connector 10 and of the complementary connector 12 (shown in FIGS. 5 and 6), the O-ring 28 and the O-ring 32 can rest on each other or can each make contact with an opposite surface of the complementary connector 12 or of the connector 10.

Figure 2:
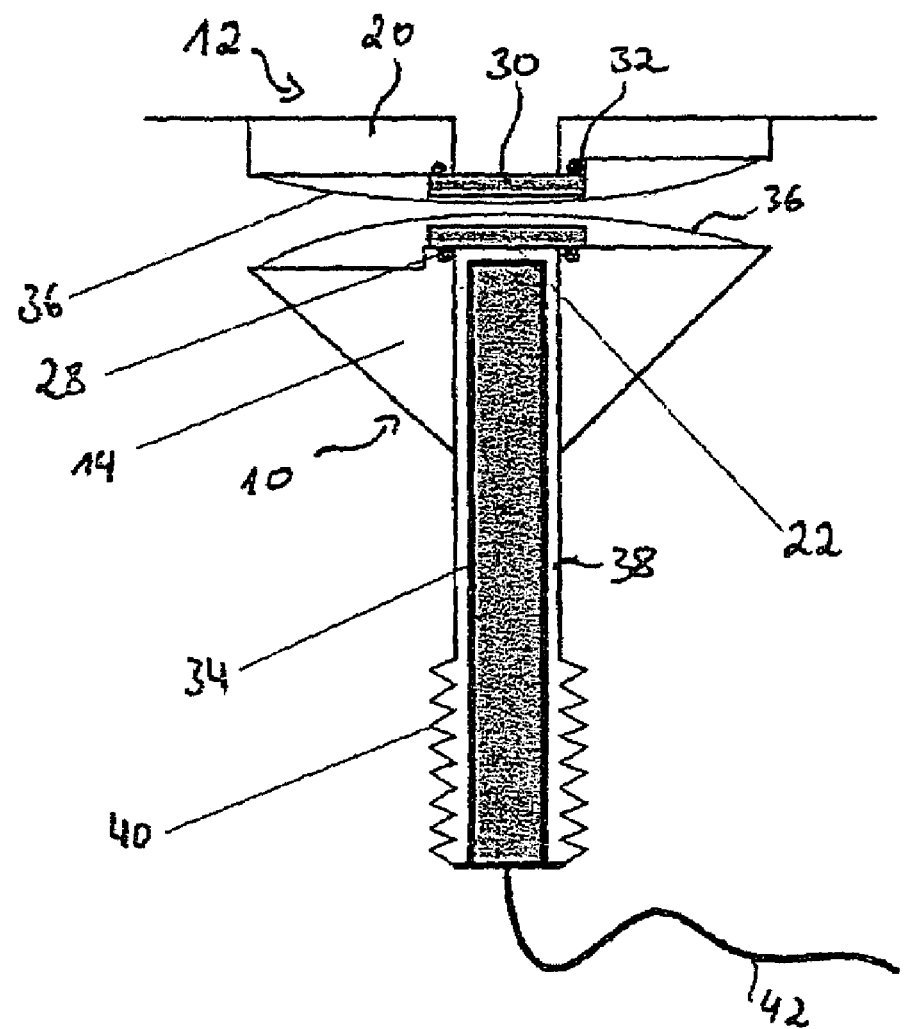
FIG. 2 shows a schematic sectional view of a preferred connector and of a complementary connector according to FIG. 1, but rotated through 90°.

FIG. 2 shows a schematic sectional view of the connector 10 and of the complementary connector 12, rotated through 900 in relation to the view of FIG. 1. Furthermore, FIG. 2 shows a sensor 34, which is not shown in FIG. 1. The sensor 34 may be, for example, a pressure, temperature or pH value sensor, etc. The sensor 34 may be designed, in particular, in order to detect or to provide conventional or particularly necessary measured values. Furthermore, a protective film 36 is illustrated in FIG. 2. The protective film 36 covers the sterile covering 22 and a partial region of the connector housing 14 or of the engagement device 16. The engagement device 16 is not illustrated in FIG. 2.

The protective film 36 can shield, for example, sections of the connector 10 or of the complementary connector 12 that are covered or overlaid by it in a sterile manner in relation to the environment. Additionally or alternatively, the protective film may be designed to protect sections of the connector 10 or of the complementary connector 12 that are covered or overlaid by it against mechanical influences, for example against impacts, etc. The protective film 36 may also be designed in order to fix components of the connector 10, for example the sterile covering 22, or to fix components of the complementary connector 12, for example the complementary, sterile covering 30. The protective film 36 may also be designed to arrange the sterile covering 22 on the connector housing 14 of the connector 10 or to arrange the complementary, sterile covering 30 on the complementary connector housing 20 of the complementary connector 12.

Furthermore, FIG. 2 illustrates a sensor chamber 38 as part of the connector housing 14. The sensor chamber 38 is designed in a partial region as an expansion bellows 40. The expansion bellows 40 permits the sensor chamber 38 to be able to be varied in its size. Furthermore, the sensor has a cable connection 42 to a peripheral device (not shown). The cable connection 42 may be a conventional signal line. However, instead of the cable connection 42, a cable-free transmission of data of the sensor 34 to a peripheral device (not shown) may also take place. Alternatively, the sensor 34 may also be equipped with an analyzing device and/or a display device, which can illustrate measured values detected by means of the sensor 34. For this purpose, the sensor 34 is advantageously at least partially designed to be essentially transparent. Similarly, the connector housing 14 can be at least partially transparent.

The covering device 22 is preferably arranged in such a manner that there is a fluidtight and a sterile connection of the covering device 22 to the connector housing 14 by means of the O-ring 28. Analogously, the complementary covering device 30 is arranged so that there is a fluidtight and a sterile connection of the complementary covering device 30 to the complementary connector housing 20 by means of the O-ring 32.

Furthermore, FIG. 2 illustrates the complementary connector 12, as described in FIG. 1.

Figure 3:
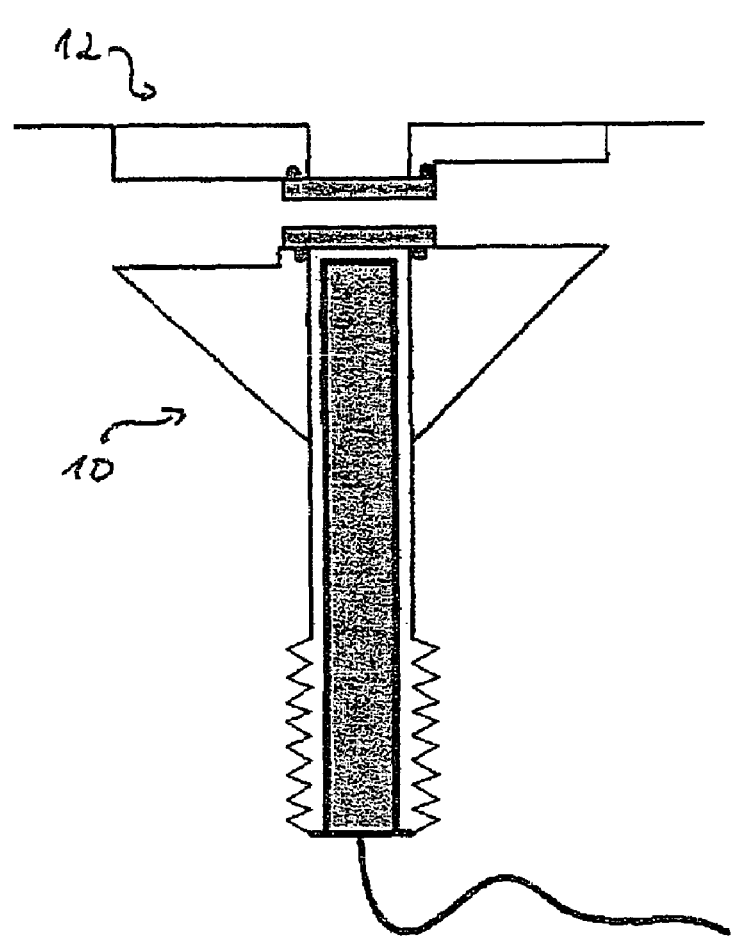
FIG. 3 shows a schematic sectional view according to FIG. 2.

FIG. 3 shows the connector 10 and the complementary connector 12, as illustrated in FIG. 2, but with the protective films 36 having been removed.

Figure 4:
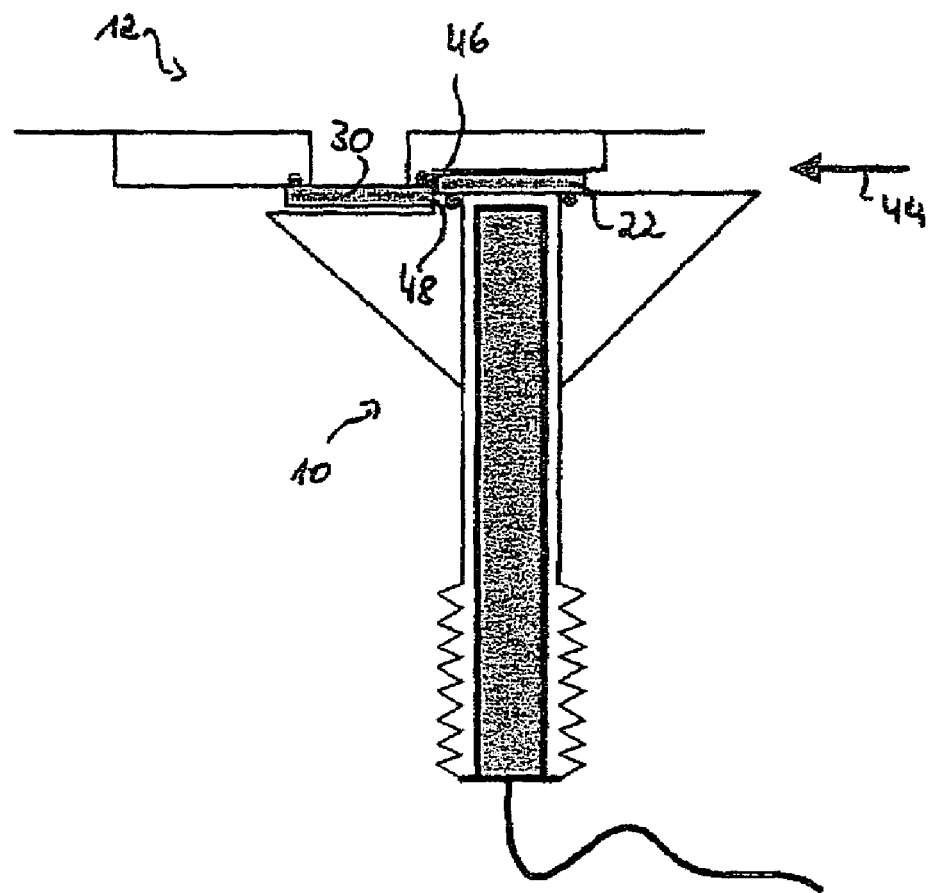
FIG. 4 shows a schematic sectional view according to FIG. 2.

FIG. 4 shows the connector 10 and the complementary connector 12, with the connector 10 and the complementary connector 12 being arranged in such manner that the engagement device 16 (not shown) and the complementary engagement device 18 (not shown) are entered into engagement. The connector 10 can be displaced relative to the complementary connector 12 along the engagement direction 44. If the connector 10 is displaced relative to the complementary connector 12, the sterile covering 22 strikes against a projection 46 of the complementary connector 12. During the movement of the connector 10 relative to the complementary connector 12 along the engagement direction 44, the sterile covering 22 remains essentially fixed in position relative to the complementary connector 12. Analogously, the sterile covering 30 of the complementary connector 12 strikes against a projection 48 of the connector housing 14 of the connector 10. During the movement of the connector 10 relative to the complementary connector 12 along the engagement direction 44, the sterile covering 30 remains essentially fixed in position relative to the connector 10, i.e. the sterile covering 30 is displaced relative to the complementary connector 12 along the engagement direction 44.

Figure 5:
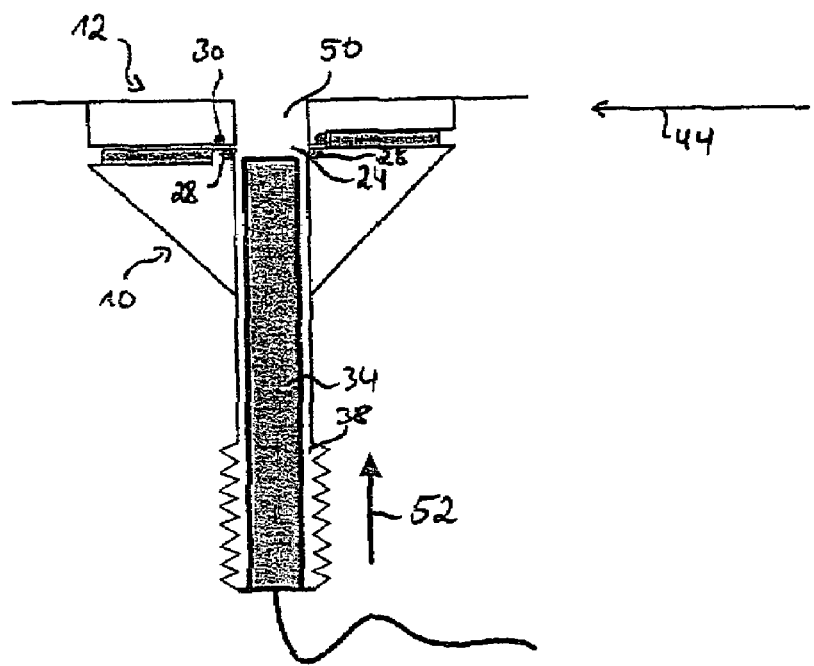
FIG. 5 shows a schematic sectional view according to FIG. 2.

FIG. 5 shows the connector 10 and the complementary connector 12 in a use position which permits the sensor 34 to be at least partially inserted through the feed-through opening 24 into the interior of the complementary connector 12. The sensor 34 is preferably displaced essentially along a sensor displacement direction 52 through an inlet opening 50 and/or an outlet opening 50 of the complementary connector. The sensor displacement direction 52, as illustrated in FIG. 5, is essentially parallel to a cylinder axis (not shown) of the essentially cylindrical sensor 34. In particular, the sensor displacement direction 52 is essentially perpendicular with respect to the engagement direction 44, as illustrated in FIG. 4.

Furthermore, the O-ring 28 and the O-ring 32 serve to provide a fluidtight connection between the feed-through opening 24 and the inlet opening/outlet opening 50. A sterile connection of the connector 10 to the complementary connector 12 can be provided by means of the two O-rings 28, 32 by the O-ring 28 entering into contact with a surface of the complementary connector 12, which surface lies opposite it. Analogously, the O-ring 32 can enter into contact with a surface of the connector 10, which surface lies opposite it. Alternatively, the O-ring 28 can also enter into contact with the O-ring 32.

The sensor 34 can be moved, in particular pressed, for example manually, into the interior of the complementary connector 12 and of the container (not shown) arranged thereon. The sensor chamber can be prestressed, for example, along the sensor displacement direction 52. For this purpose, a spring (not shown) can be arranged in or on the sensor chamber 38. In this case, the sensor 34 is advantageously moved automatically in the direction of the complementary connector 12 as soon as the connector 10 and the complementary connector 12 are in the use position. It is therefore advantageously just avoided that the connector 12 is displaced along the engagement direction 44 to such an extent that the sensor 34 can no longer be pushed into the interior of the complementary connector 12. In other words, the sensor 34 can also serve as an automatic locking device of the connector 10 and of the complementary connector 12 along the engagement direction 44.

Figure 6:
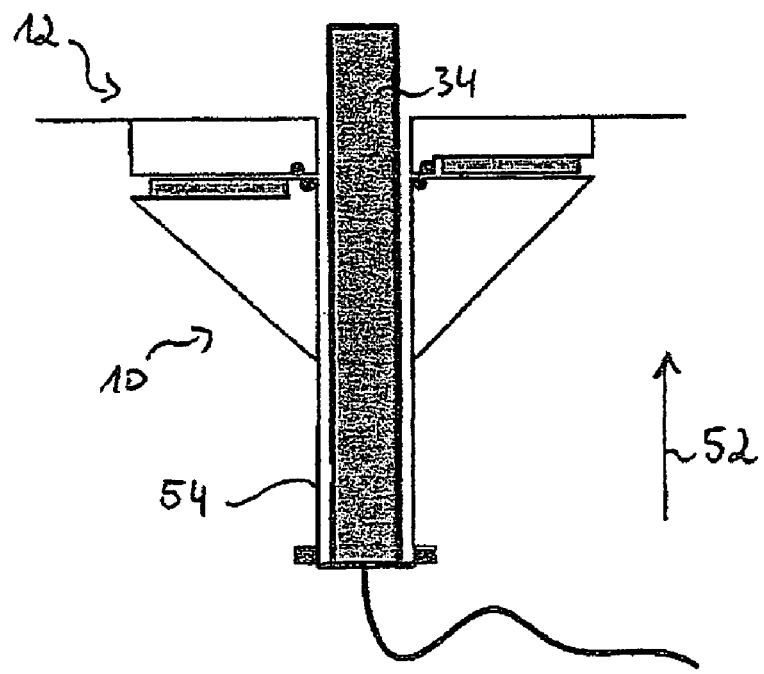
FIG. 6 shows a schematic sectional view according to FIG. 2.

FIG. 6 shows the connector 10 and the complementary connector 12 according to the use position illustrated in FIG. 5, with the sensor 34, in comparison to the illustration of FIG. 5, having been pushed or moved along the sensor displacement direction 52 and the sensor 34 at least partially protruding into the interior of the complementary connector 12 or of the container (not shown) arranged thereon.

The invention is not restricted only to the above-described exemplary embodiments. On the contrary, the invention may differ from these exemplary embodiments. For example, one or more sealing means may be arranged in the sensor chamber, as a result of which a sensor chamber wall locks to the sensor in a fluidtight manner. When the connector 10 is connected to the complementary connector 12, fluid which is located, for example, in a container cannot penetrate completely into the sensor chamber but rather merely as far as the additional O-ring. In this connection, the movement of the sensor 34 along or counter to the sensor displacement direction 52 is essentially not restricted. Similarly, a sealing means can be arranged on an inner wall of the inlet opening/outlet opening 50 of the complementary connector 12 and locks to the sensor 34 in a fluidtight manner as soon as the sensor 34 is pushed through the inlet opening/outlet opening 50. An outlet of fluid from the container can therefore also essentially be prevented as a result.

Similarly, the sensor 34 may have a different shape. The sensor 34 may be, for example, angled or round. The sensor 34 may furthermore be composed, for example, just of one or more wires, if appropriate in conjunction with one or more resistors.

Furthermore, the connector 10 can also be designed in such a manner that a fluid can flow through it. In other words, in addition to the feed-through opening 24, the connector 10 may have a further opening 54. Fluid can pass from the complementary connector 12 or the container arranged thereon into the connector 10, can flow through the connector 10 and can leave the connector 10 again through the opening 54. In particular, the opening 54 can be closed in a sterile manner by means of a covering device (not shown) or can be connected, in particular in a sterile manner, to a further device (not shown), for example a flexible tube (not shown), a container (not shown), etc. Therefore, in an advantageous manner, for example during transportation of fluid between two containers, one or more parameters of the fluid can be detected or measured by means of the sensor 34. In this case, for example, the sensor 34 can enter into contact with the fluid or the fluid can flow around it.

Furthermore, the complementary connector 12 can be an integral part of a container, and the complementary connector 12 can be, in particular, a conventional complementary connector. In other words, the connector 10 is designed in such a manner that it can be connected to a conventional connector in a fluidtight manner, and the sensor can penetrate through an opening of the conventional, complementary connector into the interior of the complementary connector or of the container arranged thereon.

Instead of the connector 10, for example, a differently designed connector 10 can be connected to the complementary connector, the differently designed connector making it possible, for example, to let a fluid out of a container. In other words, if necessary, the connector 10 according to the invention can be exchanged for a conventional connector, for example in order to close just the complementary connector 12 and/or in order to produce a fluidic connection to a further container.

Furthermore, the connector 10 can be designed in such a manner that the sensor 34 can be changed in a simple manner without the interior space 26 of the connector 10 being contaminable or rendered impure by germs or impurities from the environment. For example, the connector housing 14 may have a coupling piece and/or adapter piece, using which the sensor 34 can be changed in a simple manner.

What is claimed is:

1. A connector (10) for sterile connection to a complementary connector (12), wherein the connector (10) comprises
    a connector housing (14) with a sensor chamber (38) and with:
        an engagement device (16), which is designed such that it enters into engagement with a complementary engagement device (18) of the complementary connector (12) essentially along an engagement direction (44), and
        that, after the engagement device (16) enters into engagement with the complementary engagement device (18), the connector (10) is configured to be displaced the complementary connector (12) essentially along the engagement direction (44);
    a feed-through opening (24), for feeding a sensor device (34) through;
    a displaceable, sterile covering device (22), which is configured
        to close the feed-through opening (24) in an essentially sterile manner, and
        that, when the connector (10) is displaced relative to the complementary connector (12), the covering device (22) is displaced relative to the connector (10) essentially along the engagement direction (44),
    and with an essentially sterile sensor device (34) disposed at least partly within the sensor chamber (38), wherein
        the sensor device (34) is movable relative to the connector housing (14) essentially along a sensor displacement direction (52), and wherein
        the engagement direction (44) differs from the sensor displacement direction (52), and whereby
        the sensor chamber (38) is formed at least partly of a flexible material configured to reset and is prestressed along the sensor displacement direction (52), so that a force is transmitted to the sensor (34) and the sensor (34) is moved automatically along the sensor displacement direction and toward the complementary connector (12) as soon as the connector (10) and the complementary connector (12) are in a use position.

2. The connector (10) of claim 1, wherein the sensor chamber (38) has an essentially sterile interior, and the sensor chamber (38) contains the feed-through opening (24).

3. The connector (10) claim 2, wherein the connector housing (14) is at least partially composed of a flexible material, and the connector housing (14) is designed in such a manner that the volume of the sensor chamber (38) can be varied.

4. The connector (10) of claim 3, wherein at least part of the connector housing (14) is compressible or extendible.

5. The connector (10) of claim 3, wherein at least part of the connector housing (14) is compressible and extendible.

6. The connector (10) of claim 2, wherein the connector (10) is designed, after arrangement of the connector (10) with the complementary connector (12), to connect the sensor chamber (38) to an interior space of the complementary connector in an essentially sterile manner.

7. The connector (10) of claim 1, wherein the connector housing (14) is at least partially composed of a material capable of being reset.

8. The connector (10) of claim 1, wherein the connector housing (14) is designed to exert a force on the sensor device (34).

9. The connector (10) of claim 8, wherein the connector housing (14) is designed, after connection of the connector (10) to the complementary connector (12), to move the sensor device (34) at least partially into the complementary connector (12).

10. The connector (10) of claim 1, wherein, after removal of the covering device (22) and of the complementary covering device (30), the sensor device (34) is movable through the feed-through opening (24) into the interior space of the complementary connector (12).

11. The connector (10) of claim 1, which is designed such that a fluid can flow through it.

12. The connector (10) of claim 1, wherein the connector (10) has a further opening (54) for the passage of fluid.

13. A connector (10) for sterile connection to a complementary connector (12), the complementary connector (12) including an inlet (50) and a complementary engagement device (18), the connector (10) comprising:
    a connector housing (14) formed at least partly from a rigid material and including an engagement device (16) configured to enter into engagement with the complementary engagement device (18) of the complementary connector (12) along an engagement direction (14), the connector housing (14) having a feed-through opening (24) aligned along a displacement direction (52) substantially normal to the engagement direction (44) when the connector (10) is connected to the complementary connector (12), a sterile covering device displaceably mounted on the connector housing (14) and movable along the engagement direction (44) between a closed position where the sterile covering device (22) closes the feed-through opening (24) in an essentially sterile manner and a displaced position where the covering device (22) is displaced at least partly from the feed-through opening (24);
    a sensor chamber (38) mounted to the connector housing (14) and formed at least partly of a flexible material capable of being reset, the flexible material of the sensor chamber (38) being prestressed along the displacement direction (52); and
    a sensor device (34) mounted in the sensor chamber (38) and communicating with the feed-through opening (24) of the connector housing (14) so that the flexible prestressed material of the sensor chamber (38) exerts a force on the sensor (34) along the displacement direction (52) so that the sensor (34) is moved automatically along the displacement direction (52) and toward the complementary connector (12) as soon as the connector housing (14) is moved sufficiently in the engagement direction (44) for the feed-through opening (24) to align with the inlet (50) of the complementary connector (12).

* * * * *